United States Patent [19]

Young

[11] Patent Number: 4,758,328

[45] Date of Patent: Jul. 19, 1988

[54] SHOCK CALCINED ALUMINOSILICATE ZEOLITES

[75] Inventor: Dean A. Young, Yorba Linda, Calif.

[73] Assignee: Union Oil Company of California, Los Angeles, Calif.

[21] Appl. No.: 801,591

[22] Filed: Nov. 25, 1985

Related U.S. Application Data

[62] Division of Ser. No. 572,158, Jan. 17, 1984, Pat. No. 4,581,214.

[51] Int. Cl.$^4$ .................. C10G 47/12; C07C 2/68; C07C 5/22; C07C 5/13
[52] U.S. Cl. ........................... 208/109; 208/111; 208/134; 208/213; 208/254 H; 568/591; 585/467; 585/480; 585/481; 585/475; 585/750
[58] Field of Search ............... 585/467, 480, 481, 475, 585/750; 208/109, 111, 134; 568/591

[56] References Cited

U.S. PATENT DOCUMENTS

| | | | |
|---|---|---|---|
| 3,528,615 | 9/1970 | Kokatailo | 502/85 |
| 3,766,056 | 10/1973 | Young | 585/467 |
| 3,842,016 | 10/1974 | Young . | |
| 3,864,282 | 2/1975 | Young . | |
| 3,941,871 | 3/1976 | Dwyer et al. | 423/328 |
| 4,016,218 | 4/1977 | Haag et al. | 585/467 |
| 4,270,017 | 5/1981 | Young | 502/214 |
| 4,325,929 | 4/1982 | Young | 423/339 |
| 4,344,927 | 8/1982 | Young | 423/335 |
| 4,414,137 | 11/1983 | Young et al. | 502/162 |
| 4,433,187 | 2/1984 | Young | 585/467 |

OTHER PUBLICATIONS

Jeffrey L. Fox, "Zeolites Catalyze Patent Dispute," Science, Jan. 4, 1985, pp. 35-36.
R. von Ballmoos and W. M. Meier, "Zoned Aluminum Distribution in Synthetic Zeolite ZSM-5." Nature, vol. 289, Feb. 26, 1981, pp. 782-783.
Stephen Budiansky, "Research Article Triggers Dispute on Zeolite," Nature, vol. 300, Nov. 25, 1982, p. 309.
Lovat V. C. Rees, "When is a Zeolite Not a Zeolite?," Nature, vol. 296, Apr. 8, 1982, pp. 491-492.
C. A. Fyfe, G. C. Gobbi, J. Klinowski, J. M. Thomas, and S. Ramdas, "Resolving Crystallographically Distinct Tetrahedral Sites in Silicalite and ZSM-5 by Solid-State NMR," Nature, vol. 296, Apr. 8, 1982, pp. 530-533.
D. H. Olsen, W. O. Haag, and R. M. Lago, "Chemical and Physical Properties of the ZSM-5 Substitutional Series," Journal of Catalysts, vol. 60, 1980, pp. 390-396.

Primary Examiner—Curtis R. Davis
Attorney, Agent, or Firm—Yale S. Finkle; Gregory F. Wirzbicki; Dean Sandford

[57] ABSTRACT

A process for producing a thermally shock calcined aluminosilicate zeolite comprising (A) precalcining an aluminosilicate zeolite at a relatively low temperature, (B) very rapidly increasing the temperature of the aluminosilicate zeolite to a relatively high temperature for a short period of time, and (C) rapidly cooling the aluminosilicate zeolite. The resulting zeolite is catalytically active for hydrocarbon conversion reactions and is particularly selective for the production of para-xylene from a reaction mix of toluene and a methylating agent.

23 Claims, No Drawings

SHOCK CALCINED ALUMINOSILICATE ZEOLITES

This is a division of application Ser. No. 572,158 filed Jan. 17, 1984, now U.S. Pat. No. 4,581,214.

BACKGROUND OF THE INVENTION
1. Field of the Invention

The present invention relates to an aluminosilicate zeolite and especially to a zeolite which is catalytically active and selective in methylation reactions.
2. The Prior Art A process for the alkylation of aromatic hydrocarbons using a crystalline aluminosilicate zeolite is disclosed in U.S. Pat. No. 4,016,218. The catalyst is modified prior to use in alkylation by a thermal treatment comprising heating the catalyst to high temperatures.

Another process for the methylation of toluene to selectively produce para-xylene is described in U.S. Pat. No. 4,002,698. A phosphorus-modified aluminosilicate zeolite is used which has been activated by vapor phase treatment at a temperature between 752° F. to 1,202° F. for at least 1 hour with a methanol/water mixture.

The methylation of toluene in the presence of a steam treated, aluminosilicate zeolite has been described by Butter et al. in U.S. Pat. No. 3,965,209 which discloses a process for the selective production of para-xylene.

U.S. Pat. Nos. 3,965,207 and 3,965,208 relate to a process for the selective production of para-xylene by reacting a methylating agent with toluene in the presence of an aluminosilicate zeolite having a constraint index of from 1 to 12. Additionally, a Group VA element may be added to the catalyst described in the '208 patent.

A method of reducing the particle size of a crystalline zeolite while substantially maintaining its crystallinity is disclosed in U.S. Pat. No. 3,528,615. The zeolite is heated to an elevated temperature and thereafter the heated zeolite is quenched in a liquid medium.

It is an object of the present invention to provide an aluminosilicate zeolite for use in catalytically promoting the conversion of hydrocarbons.

Another object of the invention is to provide a catalytically active aluminosilicate zeolite that is selective for the production of para-xylene.

Yet another object of the invention is to provide a process for the production of para-xylene using catalysts containing said zeolite.

Still another object of the invention is to provide a process for producing a zeolite.

Other objects and advantages of the invention will be apparent from the following description.

SUMMARY OF INVENTION

The present invention resides in an aluminosilicate zeolite produced by shock calcination. Typically, the zeolite is prepared by a method comprising the steps of: (1) precalcining the aluminosilicate zeolite at a relatively low temperature, (2) rapidly heating the zeolite to a relatively high calcination temperature and maintaining the high calcination temperature for a relatively short period of time and (3) rapidly cooling the zeolite. When used as a catalyst for hydrocarbon conversion reactions, the zeolite is generally combined with a porous refractory oxide and, optionally, with a promoter.

The invention additionally resides in a method of alkylating an aromatic compound which comprises contacting an aromatic compound with a $C_1$ to $C_{10}$ hydrocarbon in the presence of a catalyst comprising a thermally shock calcined aluminosilicate zeolite.

DETAILED DESCRIPTION OF THE INVENTION

This invention resides in a method for thermally shock calcining an aluminosilicate zeolite and in zeolites produced by such a method, and in catalysts produced therefrom, and in a method of using such catalysts for hydrocarbon conversion reactions, particularly for alkylating an aromatic compound with a $C_1$ to $C_{10}$ hydrocarbon.

Any of the known aluminosilicate zeolites may be thermally shock calcined in accordance with the process herein to produce a catalyst which may be used in hydrocarbon conversion reactions. Thus, the L, X or Y type aluminosilicate zeolites may be thermally treated in accordance with the present invention to provide a zeolite catalyst.

The preferred zeolite is a crystalline aluminosilicate zeolite of the ZSM-5 type such as ZSM-5, ZSM-11, ZSM-12, ZSM-23, ZSM-35, ZSM-38, and the like, with ZSM-5 being preferred. ZSM-5 is a known zeolite and is more fully described in U.S. Pat. No. 3,702,886 herein incorporated by reference in its entirety; ZSM-11 is a known zeolite and is more fully described in U.S. Pat. No. 3,709,979, herein incorporated by reference in its entirety; ZSM-12 is a known zeolite and is more fully described in U.S. Pat. No. 3,832,449, herein incorporated by reference in its entirety; ZSM-23 is a known zeolite and is more fully described in U.S. Pat. No. 4,076,842, herein incorporated by reference in its entirety; ZSM-35 is a known zeolite and is more fully described in U.S. Pat. No. 4,016,245, herein incorporated by reference in its entirety; and ZSM-38 is a known zeolite and is more fully described in U.S. Pat. No. 4,046,859, herein incorporated by reference in its entirety. These zeolites are known to readily adsorb benzene and normal paraffins, such as n-hexane, and also certain mono-branched paraffins, such as 2,2-dimethylbutane, and polyalkylaromatics, such as meta-xylene. These zeolites are also known to have a crystal density not less than 1.6 grams per cubic centimeter, a silica-to-alumina ratio of at least 12, and a constraint index, as defined in U.S. Pat. No. 4,229,282, incorporated by reference herein in its entirety, within the range of 1 to 12. The foregoing zeolites are also known to have an effective pore diameter greater than 5 Angstroms and to have pores defined by 10 membered rings of oxygen atoms, as explained in U.S. Pat. No. 4,247,388 herein incorporated by reference in its entirety.

Before the aluminosilicate zeolite is subjected to thermal shock treatment, the zeolite is first precalcined at a temperature of from about 700° F. to about 1,100° F., preferably from about 700° F. to about 900° F. for about 30 minutes to about 2 days. Desirably, the thermal shock calcination of the zeolite is conducted at a temperature that is at least 300° F., preferably at least 400° F. higher than the precalcination temperature. Precalcination facilitates a rapid temperature rise during the subsequent thermal shock calcination by decreasing the heat spent in vaporizing water and desorbing volatile components. Additionally, precalcination avoids the formation of aerosols initiated by the rapid evolution of vapors within the zeolite aggregates and particles which may cause fragmentation and fluidization of the zeolite.

After the precalcination treatment, the aluminosilicate zeolite is subjected to thermal shock calcination. The thermal shock treatment of the aluminosilicate zeolite may be carried out in steam, air, ammonia, carbon dioxide, carbon monoxide or any inert atmosphere such as nitrogen, hydrogen, flue gas, argon, helium and mixtures thereof, but it is preferably effected in air. In addition, effluent gases from a combustion chamber may be utilized as a source of direct-fired heat. For maximum efficiency in transferring heat through the zeolite catalyst, the zeolite is reduced to a particle size of less than 6 mesh. At or above 7 or 8 mesh, heat transfer becomes a problem and rapid transfer of heat throughout the zeolite is difficult to achieve.

During thermal shock calcination, the aluminosilicate zeolite is subjected to a very rapid increase in temperature wherein the elevated temperature is maintained for a relatively short period of time, because prolonged exposure of the aluminosilicate zeolite to the relatively high, shock calcination temperature would destroy the original structure of the zeolite. Thus, it is critical that the temperature increase very rapidly in the thermal shock calcination of zeolites herein to prevent undesirable fusion and mineralization reactions from occurring. The zeolite is heated to a temperature within the range of from about 1,600° F. to about 2,100° F., preferably from about 1,800° F. to about 2,000° F. The zeolites herein are thermally shock calcined by relatively rapidly increasing the temperature to within the range of 1,600° F. to 2,100° F. and maintaining the zeolite at temperatures within that range for a relatively short period of time, usually from about 0.1 second to about 20 minutes, preferably from about 0.5 second to about 10 minutes, most preferably from 1 second to about 5 minutes Preferably the thermal shock calcination temperature is increased at a rate of from about 3° F. per second to about 200,000° F. per second, preferably from about 10° F. per second to about 1,000° F. per second.

One method of rapidly increasing the temperature of the aluminosilicate zeolite involves contacting a stream of preheated air with a stream of fluidized zeolite powder. The zeolite powder typically has a particle size of less than 100 microns, preferably from about 6 microns to about 100 microns, most preferably from about 25 microns to about 100 microns, and is fluidized in a flowing gas stream, for example an air stream. A zeolite powder having a particle size in this range when mixed with a gas has the characteristics of a fluid when transported through a tube or coil.

A typical apparatus for contacting the air and zeolite includes two high-temperature coils connected in series and suspended in a furnace. Air, preheated in the first coil, impinges at a right angle on a stream of fluidized aluminosilicate zeolite introduced through a tee into the second coil. The zeolite is then rapidly cooled, as by introducing a quench stream of cold air into the effluent from the second coil.

Another efficient method of rapidly heating the zeolite to the desired temperature is by blending the zeolite with a preheated solid silica sand in a sand bath.

Although the invention is not to be held to any particular theory of operation, thermally shock calcining the aluminosilicate zeolites herein is believed to alter the zeolite surface acidity by the following mechanism: electron-deficient, Lewis-acid sites form when surface hydroxyl groups combine and water is expelled. Zeolite surface protonic-acid sites Bronsted) are eliminated as Lewis-acid sites are formed. The concentration of Lewis-acid sites may decrease as thermal mobility rearranges the zeolite surface and the more active acid sites are eliminated. Thus, the thermal shock calcination of the aluminosilicate zeolites herein selectively eliminates the strongest acid sites on the zeolite surface resulting in a zeolite with slightly reduced catalytic activity but greatly enhanced selectivity. Examples of improved catalyst selectivity are the cracking of hydrocarbons to selectively produce higher proportions of intermediate molecular weight products and in alkylation reactions to the selective production of certain isomers, for example, para-xylene in the reaction of toluene with a methylating agent. The optimal thermal shock calcination temperature for the zeolite may vary according to the type of zeolite, the desired reaction, and the level of activity and selectivity desired.

After the thermal shock calcination step is completed, it is important to rapidly cool the zeolite to a temperature of about 1,000° F. or lower. Rapid cooling of the zeolite is necessary because zeolites are excellent thermal insulators and retain the high shock calcination temperatures for a period of time sufficient to cause excess sintering and loss of catalytic activity. The thermally shock calcined zeolites may be cooled, for example, by passing the thermally shock calcined zeolite through a tube immersed in a water bath or by flowing the zeolite particles over an inclined cooled metal plate or through a rotating cooled tube. Another method of rapidly reducing the temperature of the thermally shock calcined zeolites is by quenching the shock calcined zeolite in a liquid medium, such as water.

The shock calcination treatment may be performed on the zeolite alone, or if the zeolite is to be used as a catalyst, in combination with a porous refractory oxide and/or a promoter, then the treatment may be applied to composites containing such components in combination with the zeolite. In addition, the zeolite treated by shock calcination may be completely or partially cation exchanged, for example, with hydrogen, ammonium, or di- or trivalent metal cations, such as rare earth metal or alkaline earth metal cations for stability purposes or with cations of palladium, platinum, nickel, etc., to provide a hydrogenation component.

The aluminosilicate zeolites herein may be mixed with an inorganic refractory oxide in the form of clay, hydrogel or sol such as peptized boehmite alumina or colloidal silica. The inorganic refractory oxides herein are preferably selected from the group consisting of bentonite clay, boehmite alumina, silica hydrosol, colloidal silica and mixtures thereof. Other inorganic refractory oxides include alumina, silica, magnesia, beryllia, zirconia and mixtures thereof.

Normally, the aluminosilicate zeolite and inorganic refractory oxide are mixed in a weight ratio range of from about 1:10 to about 10:1, preferably from about 1:4 to about 4:1.

In order to provide suitable hydrocarbon conversion, hydrodewaxing, desulfurization and denitrogenation activity, the aluminosilicate zeolites herein may be composited with a minor amount of a promoter. The amount of promoter incorporated into the final catalyst is typically from about 0.2 to about 35 weight percent, preferably from about 0.5 to about 25 weight percent of the catalyst.

For use in hydroconversion reactions, such as hydrodesulfurization and hydrodenitrogenation processes and hydroconversion processes such as hydrocracking, hydroisomerization, reforming etc., a promoter comprising a hydrogenation component is composited or exchanged with the zeolite catalyst. Effective hydrogenation components comprise the Group VIB and Group VIII metals as disclosed in the *Periodic Table of Elements,* as published by the Sargent-Welch Scientific Company.

Hydrocarbon conversion reactions such as alkylation, isomerization, transalkylation, etc., may be promoted by compositing or exchanging the zeolite catalyst with one or more promoters selected from the group consisting of the Groups IB, IIA and VA and the rare earth elements of the *Periodic Table of Elements* as above-described and preferably compounds of phosphorus, magnesium, boron, antimony and arsenic and mixtures thereof. One especially preferred alkylation promoter is a phosphorous compound Representative phosphorus compounds include derivatives of groups represented by the formulae $PX_3$, $RPX_2$, $R_2PX$, $R_3P$, $X_3PO$, $(XO_3)P$, $R_3P=O$, $R_3P=S$, R $PO_2$, $RPS_2$, $RP(O)(OX)_2$, $RP(S)(SX)_3$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$ wherein R is alkyl or aryl and X is hydrogen, alkyl, aryl or halide. These compounds include primary, secondary or tertiary phosphines; tertiary phosphine oxides; tertiary phosphine sulfides; primary and secondary phosphonic acids and their corresponding sulfur derivatives; esters of phosphonic acids; the dialkyl alkyl phosphonates; alkyl dialkyl phosphonates, phosphinous acids, primary, secondary and tertiary phosphites and esters thereof alkyl dialkylphosphinites, dialkyl alkyl-phosphonites their esters and sulfur derivatives.

Other suitable phosphorus-containing compounds include the phosphorus halides such as phosphorus trichloride, phosphorus tribromide, phosphorus triiodide, alkyl phosphorodichlorides, dialkyl phosphorochlorides and dialkyl phosphonochloridites. Preferred phosphorus-containing compounds include phosphoric acid, phosphorus acid, and phosphate esters such as trimethylphosphate, ethylphosphate, ethylphosphite, or monophenylphosphate, etc. and mixtures thereof.

Preferred catalysts for alkylation reactions comprise about 5 to about 25 weight percent phosphorus on a support comprising silica or alumina and a shock calcined ZSM-5 zeolite, most preferably in a 1:4 to 4:1 weight ratio.

The alkylation process herein may effectively be carried out by contacting an aromatic compound and a $C_1$ to $C_{10}$ hydrocarbon with the above-described zeolite under alkylation reaction conditions.

The aromatic compound suitable for use preferably is a member selected from the group consisting of benzene, toluene, xylene, ethylbenzene, phenol, and cresol and mixtures thereof. The preferred aromatic compound is toluene.

A wide variety of $C_1$ to $C_{10}$ hydrocarbons may be used to alkylate the aromatic hydrocarbons herein. For example, the $C_1$ to $C_{10}$ alkanes, $C_2$ to $C_{10}$ olefins, as well as $C_1$ to $C_{10}$ alicyclic and alkenyl radicals and various methylating agents may be used.

In an especially preferred mode, toluene is selectively alkylated to para-xylene by contacting toluene and a methylating agent with a phosphorus-containing, thermally shock calcined aluminosilicate zeolite. The reaction is carried out at a temperature of from about 700° F. to about 1,150° F., preferably from about 800° F. to about 1,000° F., at a pressure of from about atmospheric pressure to about 250 p.s.i.a., preferably from about 15 p.s.i.a. to about 100 p.s.i.a. The molar ratio of toluene to methylating agent is normally from about 6:1 to about 1:2, preferably from about 3:1 to about 1:1

Suitable methylatin agents include methanol, methylchloride, methylbromide, dimethyl ether, methylcarbonate, dimethylsulfide, etc. The methylation reaction is accomplished using a weight hourly space velocity (WHSV) of from about 1 to 20, especially from about 2 to about 10. Para-xylene is selectively produced in the reaction; however, it should be noted that some ortho-xylene and small amounts of meta-xylene may additionally be produced. Conventional methods may be used to separate the xylene isomers or the undesirable isomers may be converted to para-xylene in an isomerization process. The methylation reaction herein may be carried out as a continuous, semi-continuous or batch type operation, using a fixed or moving type catalyst system utilizing conventional apparatus and techniques.

The invention is further illustrated by the following examples which are illustrative of various aspects of the invention and are not intended as limiting the scope of the invention as defined by the appended claims.

EXAMPLE I

Zeolite Preparation

A ZSM-5 type zeolite is prepared by mixing 1,100 ml of an alkaline solution containing sodium silicate equivalent to 4.06 moles $SiO_2$, 1.21 moles $Na_2O$, and a surfactant, 0.084 wt. % sodium dodecyloxydibenzene disulfonate, with 530 ml of an acidic solution containing aluminum sulfate equivalent to 0.051 moles $Al_2O_3$ and sulfuric acid equivalent to 0.734 moles $H_2SO_4$. The resulting gel is mixed with 202 g of an organic solution containing 0.41 moles tri-n-propylamine $(n-C_3H_7)_3N$, 0.40 moles n-propylbromide $(n-C_3H_7Br$, and 1.30 moles 2-butanone $(CH_3COC_2H_5)$. The resulting mixture is stirred and refluxed 16 hours at 190° F. Next, the vapor space is pressured to 500 psig with nitrogen and the temperature increased to 320° to 330° F. for 32 hours while stirring at 200 rpm. The solid product is collected by filtration, washed with water, exchanged with an aqueous 10 wt. % ammonium nitrate $(NH_4NO_3)$ solution, and dried at 240° F. The zeolite has a silica/alumina mole ratio of 36.5 and a residual sodium content of 0.11 wt. % $Na_2O$ after exchanging with ammonium nitrate.

EXAMPLE II

Zeolite Bonded with 30% Alumina

The dried, exchanged zeolite produced in Example I is blended with spray-dried boehmite alumina to form a powder mixture containing 30 wt. % and 70 wt. % zeolite on a water-free basis, and a combustible porosity promoter, equivalent to 10 wt. % of the zeolite composition on a dry weight basis, is added to the mixture by blending with powdered microcrystalline cellulose, manufactured by the FMC Corporation.

The above-described powdered mixture is converted into a paste by mulling with sufficient N/2 nitric acid to add 0.17 equivalents of nitric acid per mole of alumina. Next, the paste is spread into a thin layer, dried at 300° F., calcined at 900° F. for 2 hours, and then granulated into 10/30 mesh aggregates. The calcined, alumina-bonded zeolite is reexchanged by soaking for 16 hours in 2M ammonium sulfate (acid), washed with water until sulfate-free, dried at 300° F. and calcined 2 hours at 900° F.

EXAMPLE III

Precalcined 8.4 wt. % $P_2O_5$ on 70 wt. % zeolite - 30 wt. % alumina

The calcined granules (70 wt. % zeolite - 30 wt. % alumina) produced in Example II are soaked in aqueous 1.65M phosphoric acid for 30 minutes, drained, dried at 300° F. and calcined for 2 hours at 900° F. Analysis indicates that the granules contained 8.4 wt. % of phosphorus as $P_2O_5$.

EXAMPLE IV

Precalcined and shock calcined 8.4 wt. % $P_2O_5$ wt. % zeolite - 30 wt. % alumina.

A portion of the granules produced in accordance with the procedure of Example III is thermally shock calcined by spreading the granules in ⅛ inch layers in zirconia combustion boats. The boats are placed into a preheated Alundum tube. The average rate of temperature increase is 30° F./second. The temperature is held at 1,800° F. for 10 minutes. Next, the zeolite-containing granules are quenched by dumping on a cold steel plate. The resulting catalyst contained 8.4 wt. % phosphorus as $P_2O_5$.

EXAMPLE V

Precalcined 15.1 wt. % $P_2O_5$ on 70 wt. % zeolite - 30 wt. % alumina

A portion of the dried, exchanged, and calcined composite produced in accordance with the procedure of Example II is immersed in 3.2M phosphoric acid for 30 minutes, drained, dried at 300° F. and calcined for 2 hours at 900° F. The composite contained 15.1 wt. % phosphorus as $P_2O_5$.

EXAMPLE VI

Precalcined and shock calcined 15.1 wt. % $P_2O_5$ on 70 wt. % zeolite - 30 wt. % alumina.

A portion of the zeolite-containing composite produced in accordance with the procedure of Example V is thermally shock calcined by spreading the composite in granular form in ⅛ inch layers in zirconia combustion boats. The boats are placed into a preheated Alundum tube and the temperature is increased at an average rate of 30° F./second. The temperature is held at 1,800° F. for 10 minutes. Then the composites are quenched by dumping onto a cold steel plate. The resulting catalyst contained 15.1 wt. % phosphorus as $P_2O_5$.

EXAMPLE VII

Precalcined 4.0 wt. % $P_2O_5$ on 70 wt. % zeolite - 30 wt. % silica

A composite of silica bonded to a zeolite is produced by mulling for 10 minutes the zeolite produced in accordance with the procedure of Example I, with sufficient methylcellulose to add 4.3 wt. % of methylcellulose on a dry weight basis based on the weight of zeolite. The mixture thus produced is mulled with a silica sol composed of a 40 wt. % suspension of 12 nm silica particles sufficient to form a mixture of 70 wt. % zeolite and 30 wt. % silica. The mixture is spread into a thin layer, dried at 300° F., calcined at 900° F., and granulated into 10/30 mesh aggregates. Next, the above-calcined aggregates are reexchanged by soaking for 16 hours in 2M ammonium sulfate (acid), washed with water until sulfate-free, dried at 300° F. and calcined at 900° F. for 2 hours.

Phosphorus is added to the above zeolite-silica composition by soaking the composition in 3.2M phosphoric acid for 30 minutes, draining, drying at 300° F., and calcining the composition at 900° F. for 2 hours. The composition contained 70 wt. % zeolite, 30 wt. % silica and 4.0 wt. % phosphorus as $P_2O_5$.

EXAMPLE VIII

Precalcined 4.3 wt. % $P_2O_5$ on wt. % zeolite - 30 wt. % silica

A thermally shock calcined zeolite is prepared in accordance with the procedure of Example VII with the following exception:
the calcined zeolite - silica - $P_2O_5$ granules are spread in thin layers in zirconia combustion boats and placed in a preheated Alundum tube. The average temperature increase is 30° F./second and the temperature is held at 1,800° F. for 10 minutes. Next, the granules are quenched by dumping on a cold steel plate. The zeolite composition contained 70 wt. % zeolite, 30 wt. % silica and 4.3 wt. % phosphorus as $P_2O_5$

EXAMPLE IX to XIV

Toluene is selectively methylated to para-xylene by feeding a 2:1 molar ratio of toluene and methanol respectively into a reactor containing the zeolite catalysts described in Table 1 below. The toluene and methanol are fed into the reactor at atmospheric pressure, a temperature of 1,100° F. and a weight hourly space velocity (WHSV) of 10. The catalysts used and results are described and summarized in Table 1 below:

TABLE 1

| Ex. | Zeolite used | Precalcination °F. | Precalcination Hrs. | Shock Calcination °F. | Shock Calcination Min. | Hours on Stream | Toulene Conversion Wt. % | Selectivity for Xylene Production Wt. % | Xylene Isomers P | Xylene Isomers M | Xylene Isomers O | Yield P-Isomer Wt. %* |
|---|---|---|---|---|---|---|---|---|---|---|---|---|
| IX | Ex. III | 900 | 2 | — | — | 5.5 | 39 | 88 | 29 | 51 | 20 | 11 |
| X | Ex. IV | 900 | 2 | 1,800 | 10 | 5.5 | 34 | 92 | 38 | 44 | 18 | 14 |
| XI | Ex. V | 900 | 2 | — | — | 4.5 | 32 | 95 | 59 | 26 | 15 | 21 |
| XII | Ex. VI | 900 | 2 | 1,800 | 10 | 5 | 35 | 97 | 66 | 21 | 13 | 26 |
| XIII | Ex. VII | 900 | 2 | — | — | 4.5 | 38 | 91 | 36 | 43 | 21 | 14 |
| XIV | Ex. VIII | 900 | 2 | 1,800 | 10 | 4.5 | 34 | 91 | 62 | 27 | 11 | 22 |

*The yield is calculated as Wt. % P-xylene based on the toluene feed.

The above data prove that the catalysts containing the thermally shock calcined zeolites (Example IV, VI and VIII) are more selective to the production of para-xylene as compared to the otherwise identical catalysts that do not contain a thermally shock calcined zeolite (Examples III, V and VII). Also, the catalysts of Examples IV and VI evidence greater selectivity for xylene production than the catalysts of Examples III and V, respectively.

Obviously, many modifications and variations of the invention, as herein before set forth, may be made without departing from the spirit and scope thereof, and only such limitations should be imposed as are indicated in the appended claims.

I claim:

1. A hydroconversion process comprising contacting a hydroconversion feedstock under hydroconversion reaction conditions with a catalyst to convert said feedstock via hydroconversion reactions into hydroconversion reaction products, said catalyst comprising a zeolite prepared by a process comprising:
    (a) precalcining an aluminosilicate zeolite at a temperature below the temperature to which the zeolite is heated in step (b) but sufficiently high to vaporize water and desorb volatile components;
    (b) thermally shock calcining the precalcined aluminosilicate zeolite by rapidly increasing the temperature of said precalcined zeolite at a rate between about 3° F./second and about 200,000° F./second to a relatively high temperature between about 1600° F. and about 2100° F. and maintaining said relatively high temperature for a period of time between about 0.1 second and about 20 minutes, said period of time being sufficiently short to avoid substantial sintering; and
    (c) cooling the thermally shock calcined aluminosilicate zeolite at a rate sufficiently rapid to avoid substantial sintering and substantial loss of catalytic activity from said shock calcining.

2. A process as defined by claim 1 wherein said hydroconversion process is selected from the group consisting of hydrodesulfurization, hydrodenitrogenation, hydrocracking, hydroisomerization and reforming.

3. A process for alkylating an aromatic compound which comprises contacting said aromatic compound with a $C_1$ to $C_{10}$ hydrocarbon under alkylation reaction conditions in the presence of an alkylation catalyst comprising a zeolite prepared by a process comprising:
    (a) precalcining an aluminosilicate zeolite at a temperature below the temperature to which the zeolite is heated in step (b) but sufficiently high to vaporize water and desorb volatile components;
    (b) thermally shock calcining the precalcined aluminosilicate zeolite by rapidly increasing the temperature of said precalcined zeolite at a rate between about 3° F./second and about 200,000° F./second to a relatively high temperature between about 1600° F. and about 2100° F. and maintaining said relatively high temperature for a period of time between about 0.1second and about 20 minutes, said period of time being sufficiently short to avoid substantial sintering; and
    (c) cooling the thermally shock calcined aluminosilicate zeolite at a rate sufficiently rapid to avoid substantial sintering and substantial loss of catalytic activity from said shock calcining.

4. A process as defined by claim 3 wherein said aromatic compound is selected from the group consisting of benzene, toluene, xylene, ethylbenzene, phenol, cresol and mixtures thereof.

5. A process as defined by claim 4 wherein said $C_1$ to $C_{10}$ hydrocarbon is selected from the group consisting of $C_1$ to $C_{10}$ alkanes and $C_2$ to $C_{10}$ olefins.

6. A process as defined by claim 3 wherein said precalcination temperature is about 400° F. or more below said relatively high thermal shock calcination temperature.

7. A process as defined by claim 3 wherein the temperature of said precalcined aluminosilicate zeolite in step (b) is increased to said relatively high temperature at a rate between about 10° F./second and about 1000° F./second and maintained at said relatively high temperature for a period of time between about 0.5 second and about 10 minutes.

8. A process as defined by claim 3 wherein the temperature of said precalcined aluminosilicate zeolite in step (b) is increased to a relatively high temperature between about 1800° F. and 2000° F. and maintained at said relatively high temperature for a period of time between about 1.0 second and about 5 minutes.

9. A process as defined by claim 3 wherein said aluminosilicate zeolite is precalcined at a temperature in the range between about 700° F. and about 1100° F.

10. A process as defined by claim 3 wherein said aluminosilicate zeolite is precalcined at a temperature in the range between about 700° F. and about 900° F.

11. A process as defined by claim 3 wherein said thermally shock calcined aluminosilicate zeolite is rapidly cooled to a temperature below about 1000° F.

12. A process as defined by claim 11 wherein said thermally shock calcined aluminosilicate zeolite is rapidly cooled to a temperature below about 1000° F. by passing the thermally shock calcined aluminosilicate zeolite through a tube immersed in water.

13. A process as defined by claim 11 wherein said thermally shock calcined aluminosilicate zeolite is rapidly cooled to a temperature below about 1000° F. by contacting the thermally shock calcined aluminosilicate zeolite with a stream of cold air.

14. A process as defined by claim 11 wherein said thermally shock calcined aluminosilicate zeolite is rapidly cooled to a temperature below about 1000° F. by flowing the thermally shock calcined aluminosilicate zeolite over an inclined, cooled metal plate.

15. A process as defined by claim 11 wherein said thermally shock calcined aluminosilicate zeolite is rapidly cooled to a temperature below about 1000° F. by quenching the thermally shock calcined aluminosilicate zeolite in a liquid medium.

16. A process as defined by claim 11 wherein said thermally shock calcined aluminosilicate zeolite is rapidly cooled to a temperature below about 1000° F. by passing the thermally shock calcined aluminosilicate zeolite through a rotating cooled tube.

17. A process as defined by claim 3 wherein said aluminosilicate zeolite comprises a crystalline aluminosilicate zeolite of the ZSM-5 type.

18. A process as defined by claim 3 wherein said alkylation catalyst further comprises an inorganic refractory oxide component.

19. A process as defined by claim 18 wherein said alkylation catalyst further comprises a phosphorus component.

20. A process for selectively producing para-xylene which comprises contacting toluene with a methylating agent under methylation reaction conditions in the presence of a methylation catalyst comprising a zeolite prepared by a process comprising:
    (a) precalcining an aluminosilicate zeolite at a temperature below the temperature to which the zeolite is heated in step (b) but sufficiently high to vaporize water and desorb volatile components;
    (b) thermally shock calcining the precalcined aluminosilicate zeolite by rapidly increasing the temperature of said precalcined zeolite at a rate between about 3° F./second and about 200,000° F./second to a relatively high temperature between about 1600° F. and about 2100° F. and maintaining said relatively high temperature for a period of time between about 0.1 second and about 20 minutes, said period of time being sufficiently short to avoid substantial sintering; and (c) cooling the thermally shock calcined aluminosilicate zeolite at a rate sufficiently rapid to avoid substantial sintering and substantial loss of catalytic activity from said shock calcining.

21. A process as defined by claim 20 wherein said methylating agent is selected from the group consisting of methanol, methylchloride, methylbromide, dimethyl ether, methylcarbonate and dimethylsulfide.

22. A process as defined by claim 20 wherein said methylation catalyst further comprises alumina and a phosphorus component.

23. A process as defined by claim 22 wherein said phosphorus component is selected from the group consisting of phosphoric acid, phosphorus acid, phosphate esters and mixtures thereof.

* * * * *